United States Patent [19]
Kim et al.

[11] Patent Number: 5,897,860
[45] Date of Patent: Apr. 27, 1999

[54] METHOD FOR CONTROLLING BLEEDING AND MICROBIAL INFECTIONS BY ADMINISTERING THROMBIN, CASEIN KINASE II, AND SPHINGOSINE

[75] Inventors: Seung-Ho Kim, Taejon; Jin Young Lee, Kyungki-do; Moon Hi Han, Taejon, all of Rep. of Korea

[73] Assignee: Korea Institute of Science Technology, Seoul, Rep. of Korea

[21] Appl. No.: 08/716,198

[22] PCT Filed: Dec. 30, 1995

[86] PCT No.: PCT/KR95/00189

§ 371 Date: Sep. 30, 1996

§ 102(e) Date: Sep. 30, 1996

[87] PCT Pub. No.: WO96/23523

PCT Pub. Date: Aug. 8, 1996

[30] Foreign Application Priority Data

Feb. 3, 1995 [KR] Rep. of Korea ............. 1995/1949
Feb. 25, 1995 [KR] Rep. of Korea ............. 1995/3751
Nov. 2, 1995 [KR] Rep. of Korea ............. 1995/39458

[51] Int. Cl.$^6$ ............. A61K 38/43; A61K 38/54; A61K 38/48; A61K 31/685
[52] U.S. Cl. ............. 424/94.2; 424/94.1; 424/94.64; 424/94.63; 514/76; 514/834; 514/925
[58] Field of Search ............. 424/94.2, 94.63, 424/94.64, 283.1, 94.1; 514/76, 834, 925

[56] References Cited

U.S. PATENT DOCUMENTS 4,952,683  8/1990  Tschannen et al. ............. 536/18.6
5,151,360  9/1992  Handa et al. ............. 435/375

OTHER PUBLICATIONS

Eriksson et al., Endothelial cells release casein kinase II–like activity capable of phosphorylating fibrinogen in response to thrombin, Thromb. Res. 72:315–320, 1993.

Guyton, Human Physiology and Mechanisms of Disease, 4th ed., W.B. Saunders and Company, Philadelphia, PA, Chapter 21, p. 220, 1987.

Thrombosis Research 61, pp. 243–252, (1991) Article "The Effects of in Vitro Phosphorylation and Dephosphorylation on the Thrombin–Induced Gelation and Plasmin Degradation of Fibrinogen" / Martin, et al.

Archives of Biochemistry and Biophysics, vol. 241, No. 1, Aug. 15, 1985, pp. 225–231, Article: "Phosphorylation in Vitro of Fibrinogen from Three Mammalian Species with Four Different Protein Kinases" / Humble, et al.

Biochemistry and Biophysical Research Communications, vol. 117, No. 2, Dec. 16, 1983, pp. 631–636, Article: "Phosphorylation of Fibrinogen by Casein Kinase" / Itarte, et al.

Biochemistry and Biophysical Research Communications, vol. 96, No. 4, Oct. 31, 1980, pp. 1503–1507, Article: "Phosphorylation of Human Fibrinogen in Vitro with Cyclic 3', 5'–AMP–Stimulated Protein Kinase and ($^{32}$p) APT"/ Engström, et al.

The Journal of Biophysical Chemistry, vol. 266, No. 32, Nov. 13, 1991, pp. 21773–21776, Article: "Activation of Casein Kinase II by Sphingosine" / McDonald, et al.

Thrombosis Research 53, pp. 1–9, (1989) Article "Dephosphorylation of Human Fibrinogen Previously Phosphorylated in Vitro by Protein Kinase C, by Whole Blood or Intestinal Alkaline Phosphatase Effects on Thrombin–Induces Gelation of in Vitro Dephosphorylated Human Fibrinogen" / Forsberg.

Febs Letters, vol. 143, No. 4, (Jul. 1992) pp. 199–204, Article "Phosphorylation of Human Fibrinogen in Vitro with Calcium–Activated, Phospholipid–Dependent Protein Kinase and [$^{32}$P]ATP" / Papanikolaou.

Primary Examiner—David M. Naff
Assistant Examiner—Janet M. Kerr
Attorney, Agent, or Firm—McAulay Nissen Goldberg Kiel & Hand, LLP

[57] ABSTRACT

The present invention relates to a hemostatic composition comprising at least 0.1 NIH U/ml of thrombin, about 0.01 mU/ml of casein kinase II, and from 10 ng/ml to 100 ng/ml of sphingosine or a sphingosine derivative. The composition is effective in treating patients suffering from hemophilia, ulcers, or microbial infections. In addition, the composition is effective in reducing clotting time during the surgical procedure of suturing blood vessels.

9 Claims, 2 Drawing Sheets

METHOD FOR CONTROLLING BLEEDING AND MICROBIAL INFECTIONS BY ADMINISTERING THROMBIN, CASEIN KINASE II, AND SPHINGOSINE

BACKGROUND OF THE INVENTION

1. Field of the Invention

The present invention is related to a novel hemostatic composition. More specifically, the present invention is related to a hemostatic composition comprising thrombin, casein kinase II, and sphingosine or a sphingosine derivative and providing rapid clotting and hemostasis.

2. Description of the Prior Arts

Hemostasis involves three complex mechanisms: clot formation, rapid constriction of the injured blood vessel and the aggregation of platelets to form a plug on the injured surface of the blood vessel. A clot is formed by a series of transformations involving more than ten different proteins, calcium ion (Ca2+) and thromboplastin. When bleeding occurs, fibrinogen, which is highly soluble, is converted into insoluble fibrin monomer by the proteolytic action of thrombin. The fibrin monomers spontaneously associate to form a clot, on which factor XIIIa acts to aggregate platelets to form a plug on the injured surface of the blood vessel.

It has been reported that phosphate groups attached to fibrinogen affect the gelation of thrombin (Forsberg, P. O., Thromb. Res., 53, 1–9, 1989). And, various protein kineses such as protein kinase A (Engstrim, L., Edlund B., Rangnarsson, U., Dahlqvist-Edberg, U., and Humble, E., Biochem. Biophys. Res. Commun., 96, 1507, 1980), protein kinase C, casein kinase I (Itarte, E., Plana, M., Guasch, M. D., and Martos, C., Biochem. Biophys, Res. Commun., 117, 631–636, 1983), and casein kinase II (Humble, E., Heldin, P., Forsberg, P. O. and Engstrom, L., Arch. Biochem. Biophys., 241, 225–231, 1985) have been reported to be involved in the phosphorylation of fibrinogen. The effect of the phosphorylation of fibrinogen on the thrombin-induced gelation of fibrinogen varies depending on thekinase used to phosphorylate fibrinogen. The phosphorylated fibrinogen is ineffeciently cleaved by plasmin regardless of the kind of the kinase involved in the phosphorylation thereof (Martin, S. C., et al., Thromb. Res. 61, 243252, 1991).

Sphingosine, which is one kind of sphingolipid, has important roles in the growth and differentiation of cells. Further, sphingosine also is reported to have an ability to increase the activity of casein kinase II (McDonald, O.Bradley; Hannun, Yusuf A.; Reynolds, E. Hugh and Sahyoun, Naji, Journal of Biological Chem., Vol. 266, No. 32, pp 21773–21776, 1991).

A property required to serve as an efficient hemostatic agent is fast control of bleeding in order to prevent entry of pathogens at the bleeding site or massive hemorrhage during operations. Thrombin preparations have been most widely employed as commercially available hemostatic compositions.

The inventors conducted extensive studies to develop a more efficient hemostatic composition, which allows a faster hemostasis than conventional hemostatic compositions. As a result thereof, they surprisingly found that, if the thrombin-containing hemostatic compositions contains casein kinase II, a protein phosphorylation enzyme, together with sphingosine or a sphingosine derivative, it can exhibit its hemostatic activity in a shorter period of time.

SUMMARY OF THE INVENTION

Thus, an object of the present invention is to provide a hemostatic composition comprising particular additives which can promote formation of fibrin clots.

This object of the present invention can be accomplished by a hemostatic composition comprising thrombin, casein kinase II, and sphingosine or a sphingosine derivative.

BRIEF DESCRIPTION OF DRAWINGS

This invention will be described in more detail with reference to the accompanying drawings in which.

Figure 1:
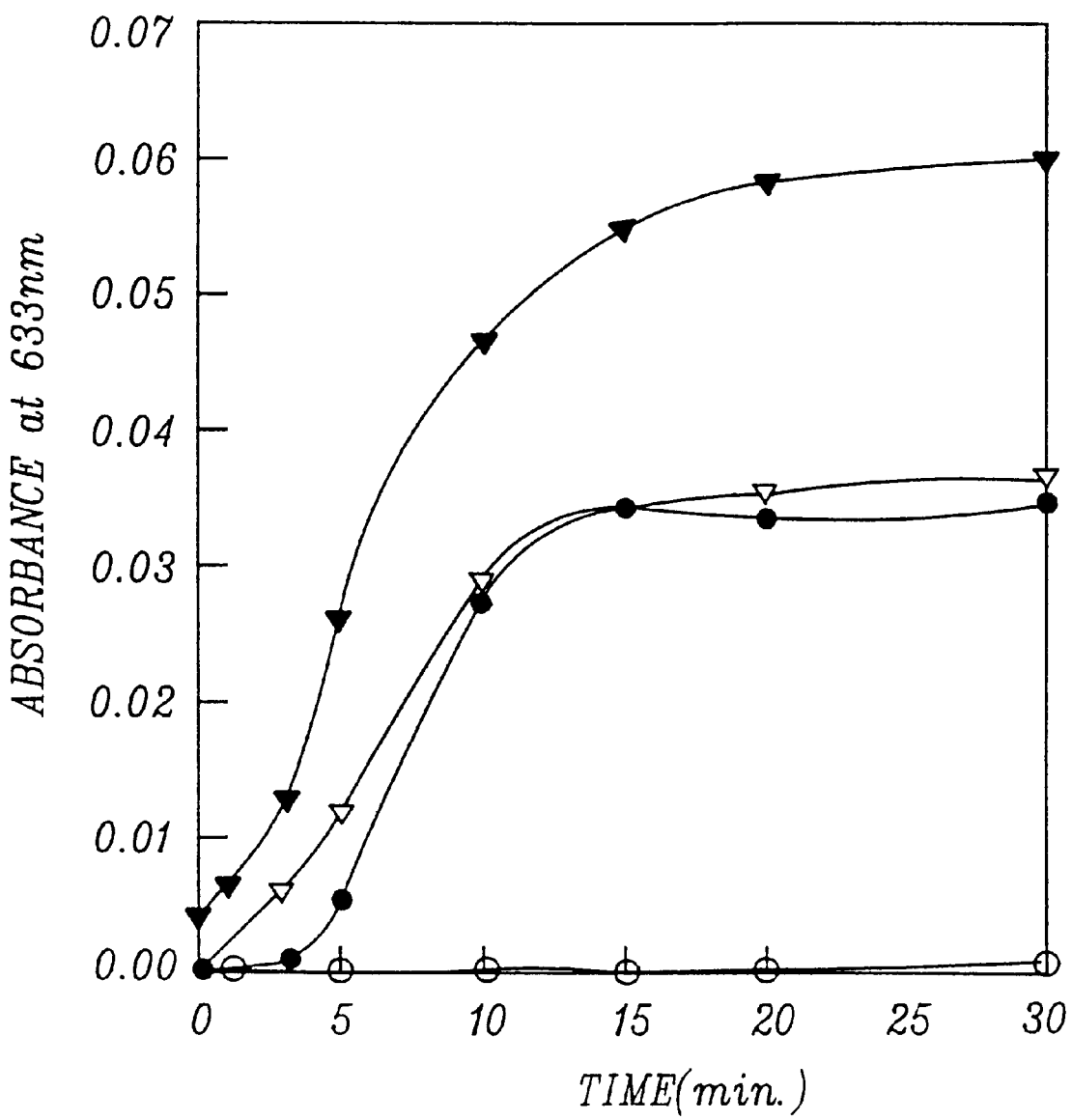
FIG. 1 is a graph showing hemostatic activities of hemostatic compositions containing various materials, in which the line -○- indicates a fibrinogen solution; the line -●- indicates a fibrinogen solution containing thrombin; the line -▽- indicates a fibrinogen solution containing casein kinase II plus thrombin; and the line -▼- indicates a fibrinogen solution containing sphingosine, casein kinase II, and thrombin.

The above and other objects, features and applications of the present invention will be apparent to one of ordinary skill in the art from the following detailed explanation.

DETAILED EXPLANATION OF THE INVENTION

A hemostatic composition according to the present invention comprises thrombin, casein kinase II, and sphingosine or a sphingosine derivative.

In the present invention, casein kinase II, a protein phosphorylation enzyme, acts to phosphorylate amino acids of fibrinogen. The phosphorylated fibrinogen is more prone to be converted into fibrin by the action of thrombin.

When sphingosine or a sphingosine derivative is incorporated into the composition comprising thrombin and casein kinase II, the former enhances the activity of casein kinase II and thrombin, and the composition can stop bleeding in a shorter period of time than the composition without sphingosine or a sphingosine derivative.

The sphingosine derivatives may include, but are not limited to, O-phosphorylethanol amine, sphingomyelin, glucosyl sphingosine, galactosyl sphingosine, sphingosine phosphates, erythrosphingenines, threosphingenines, stearoylsphingomyelin, ceramides, ceramide dihexosides, ceramide tetrahexosides, asialogangliosides, disialogangliosides, trisialogangliosides, monosialogangliosides, and the like. These sphingosine derivatives may be used individually or as mixtures thereof.

The amount of thrombin incorporated into the composition according to the present invention may be more than 0.1 NIHU/ml. The unit of thrombin, "NIHU", means a United States (US) National Institute of Health (NIH, Bethesda, USA) standard unit, and one "NIHU" is equivalent to 1.1 to 1.3 IU of thrombin.

The amount of casein kinase II incorporated into the composition according to the resent invention may be in the range from 0.01 mU/ml to 1 mU/ml, and is preferably about 0.1 mU/ml based on the total amount of the composition. One (1) unit of casein kinase II is defined as the enzyme activity which catalyzes the transfer of 1 μmole phosphate from ATP to a substrate at 37° C. in 1 minute.

The amount of sphingosine or its derivative incorporated into the composition according to the present invention may be in the range from 0.01 μg/ml to 0.1 μg/ml, and is preferably about 0.05 μg/ml based on the total amount of the composition.

The composition according to the present invention can be formulated into various preparations, for example tablets, capsules, powders, solutions, suspensions and the like, according to the conventional techniques well known to those skilled in the pharmaceutical industries.

The composition according to the present invention can be administered by various routes depending on the purpose, target site or type of its formulations, which can be easily chosen by those skilled in the art.

The composition of the present invention can be used for hemostasis or hemopexis outside the living body as well as inside the living body, for example in treating an ulcer. Further, it can be used to treat hemophilia, or as an aid for treating hemophilia. Moreover, it can be used as a hemostatic composition as well as an aid for conventional hemostatic compositions. It also can be used to suture an injured blood vessel, as well as an inhibitor of the growth of bacteria, fungi, or virus.

The degree of fibrin clotting caused by the action of the composition of the present invention is calculated by measuring the changes in the light absorbance of the mixtures of fibrinogen solution and the composition. The absorbance is measured using an UV/VIS spectrophotometer. And, the agglutination activity of the composition can be observed with naked eyes by mixing blood plasma of human being and the composition of the invention in accordance with the Lee-White method.

PREFERRED EMBODIMENTS OF THE INVENTION

The present invention will be further described by way of the following examples. However, these examples are provided for illustration purposes only and should not be construed as limiting the scope of the invention, which is properly delineated in the accompanying claims. The parts or percents in Examples are based on the weight, unless indicated otherwise.

EXAMPLE 1

Fibrinogen (CalBiochem, USA) (24 mg) was dissolved into a mixture (100 ml) of 100 mM phosphate buffered saline (pH 7.4) and 12 mM $MgCl_2$ and the resulting solution was evaporated to a final concentration of 1.2 mg fibrinogen/ml. $MgCl_2$ and ATP were added to 5 ml of the fibrinogen solution to the concentrations of 12 mM and 1 mM, respectively to give a substrate solution.

Thrombin (Sigma, USA) and casein kinase-II (Boehringer Mannheim, Germany) were diluted with 100 mM phosphate buffered saline (pH 7.4) to the concentrations of 1 NIHU/ml and 1 mU/ml, respectively. Sphingosine (Sigma, USA) was dissolved into a minimum amount of ethanol and diluted with 100 mM phosphate buffered saline to a concentration of 0.1 mg/ml.

In order to measure the fibrin clot formed by thrombin or the composition of the invention, four samples were prepared: 1̂ fibrinogen solution 0.7 ml; 2̂ fibrinogen solution 0.7 ml+thrombin solution 0.1 ml (final concentration 0.1 NIHU/ml); 3̂ fibrinogen solution 0.7 ml+thrombin solution 0.1 ml (final concentration 0.1 NIHU/ml)+casein kinase-II solution 0.1 ml (final concentration 0.1 mU/ml); and 4̂ fibrinogen solution 0.7 ml+thrombin solution 0.1 ml (final concentration 0.1 mU/ml)+casein kinase II solution 0.1 ml (final concentration 0.1 mU/ml)+sphingosine (final concentration 10 μg/ml). 50 mM phosphate buffered saline (pH 7.4) was added to these samples to make the final volume of all the samples to 1 ml.

These samples were reacted at 37° C. and the absorbencies at 633 nm were measured by using a UV/VIS spectrophotometer (Beckmann Model No. DU-70, USA) at 0, 5, 10, 15, 20, 25 and 30 minutes.

The results are shown in FIG. 1. In FIG. 1, the line -○- indicates the fibrinogen solution; the line -●- indicates the fibrinogen solution containing thrombin; the line -▽- indicates the fibrinogen solution containing casein kinase II plus thrombin; and the line -▼- indicates the fibrinogen solution containing sphingosine, casein kinase II, and thrombin.

As can be seen from FIG. 1, the fibrinogen solution containing sphingosine, casein kinase II and thrombin forms a larger amount of fibrin clot than the fibrinogen solutions containing thrombin in single, or containing thrombin and casein kinase II.

EXAMPLE 2

In order to estimate the blood coagulation activity of the composition of the invention, the same materials used in Example 1 were employed, except two kinds of buffer solutions were used; the buffer "A" is 50 mM phosphate buffered saline (pH 7.4) and the buffer "B" is 50 mM phosphate buffered saline (pH 7.4) containing 1 mM ATP and 12 mM $MgCl_2$. Each of the following samples (2) to (7) was adjusted to have a final concentration of 0.02 mM ATP.

A blood coagulation activity of the samples was measured by a modified Lee-White method. That is to say, seven test tubes (1) to (7) each containing 1.5 ml of human blood sample were prepared, and 0.1 ml of one of the following samples (1) to (7) was added to each test tube: Sample No. 1, the buffer "A"; sample No. 2, a mixture of buffer "A" (0.4 ml), buffer "B"(0.2 ml) and thrombin solution (0.2 ml); sample No. 3, a mixture of buffer "A" (0.2 ml), buffer "B" (0.2 ml), thrombin solution (0.2 ml) and casein kinase II solution (0.2 ml); sample No. 4, a mixture of buffer "A" (0.2 ml), buffer "B" (0.2 ml), thrombin solution (0.2 ml) and sphingosine solution (0.2 ml); sample No. 5, a mixture of buffer "B" (0.2 ml), thrombin solution (0.2 ml), casein kinase II solution (0.2 ml) and sphingosine solution (0.2 ml); sample No. 6, a mixture of buffer "A" (0.4 ml), buffer "B" (0.2 ml), sphingosine solution (0.2 ml); and sample No. 7, a mixture of buffer "A" (0.2 ml), buffer "B" (0.2 ml), casein kinase II solution (0.2 ml) and sphingosine solution (0.2 ml).

Test tubes were allowed to stand at room temperature. After 10 minutes, test tubes were declined to observe coagulation of blood. Test tube Nos. 1, 6 and 7 showed no coagulation, while test tube Nos. 2 to 5, which contain thrombin, showed coagulation. Among them, in particular the test tube No. 5 containing the composition of the invention showed the fastest coagulation of blood.

Figure 2:
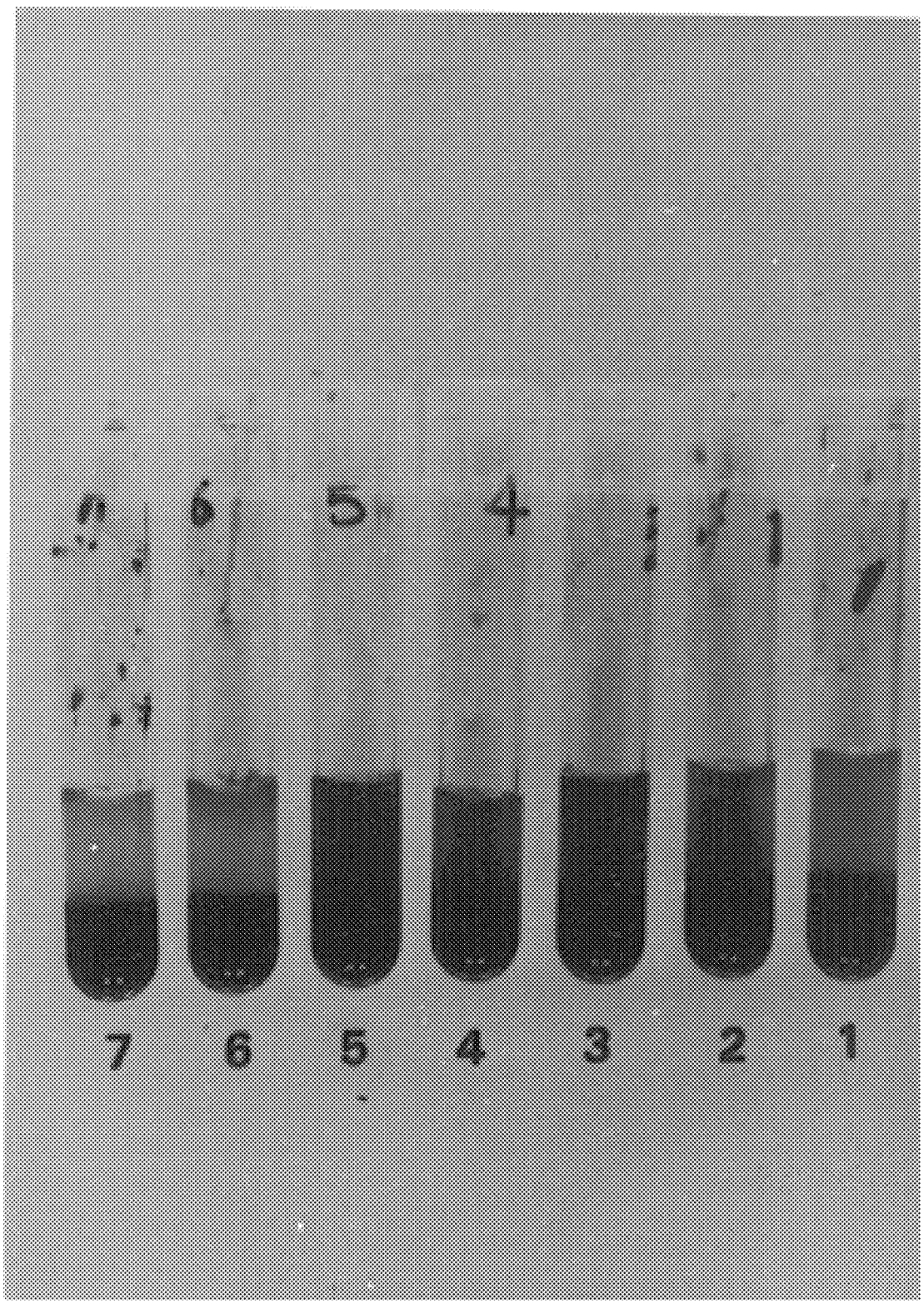
FIG. 2 shows blood coagulation activities of the compositions containing various materials, in which test tube No. 1 contains a buffer "A"; test tube No. 2 contains a mixture containing buffer "A" (0.4 ml), buffer "B" (0.2 ml) and thrombin solution (0.2 ml); test tube No. 3 contains a mixture of buffer "A" (0.2 ml), buffer "B" (0.2 ml), thrombin solution (0.2 ml) and casein kinase II solution (0.2 ml); test tube No. 4 contains a mixture of buffer "A" (0.2 ml), buffer "B" (0.2 ml), thrombin solution (0.2 ml) and sphingosine solution (0.2 ml); test tube No. 5 contains a mixture of buffer "B" (0.2 ml), thrombin solution (0.2 ml), casein kinase II solution (0.2 ml) and sphingosine solution (0.2 ml); test tube No. 6 contains a mixture of buffer "A" (0.4 ml), buffer "B" (0.2 ml), sphingosine solution (0.2 ml); and test tube No. 7 contains a mixture of buffer "A" (0.2 ml), buffer "B" (0.2 ml), casein kinase II solution (0.2 ml) and sphingosine solution (0.2 ml). Each sample was used in an amount of 0.8 ml.

And, when the test tubes were centrifuged at 1,000 rpm for five minutes, test tube Nos. 1, 6 and 7 showed a complete separation of plasma from the precipitated blood cells, while test tube Nos. 2 to 5 showed a slight or no separation. In particular, test tube No. 5 containing the composition of the invention showed no separation at all. These results are shown in FIG. 2.

EXAMPLE 3

In order to measure the thrombin clotting time of the composition of the invention, 0.4 ml of plateletrich plasma was placed into seven test tubes (10×75 mm), to each of which one of the seven samples of Example 2 was added in an amount of 0.1 ml. The test tubes were well shaken and the time required to form a fibrin clot was measured. The test tube No. 5 formed a fibrin clot within 2 minutes+20 seconds, while the test tube No. 2 formed fibrin clots within 10 minutes+30 seconds.

Therefore, the composition of the invention formed fibrin clots about five times as fast as the comparative compositions.

EXAMPLE 4

Acute toxicity

The composition of the present invention, which was prepared in Example 1, was intraperitoneally administered to ten ICR mice (five males plus five females) in an amount of 10 ml/kg. During seven days after the administration, the number of dead animals and the behavior of the animals were observed. Seven days after the administration, the animals were sacrificed and autopsied to observe the organs with naked eyes. The results are summarized below.

1) There was no died animal and the animals' behaviors were normal during seven days after the administration.

2) Autopsy opinion

Skin: Normal

Eyes: Normal

Liver: Normal

Spleen: Normal

Kidney: Normal

Digestive organs: Normal

Genital and urinary organs: Normal

Heart: Normal

Lung: Normal

Chest: Normal

EXAMPLE 5

Two mice were injured with a syringe at the coronary artery so that the artery bled, and the injured part of each mouse was covered with a cotton soaked with the inventive composition (Inventive) or thrombin solution (Control) of Example 1 for 2 minutes. The bleeding of the wounded part of the mouse of inventive group was stopped as well as the artery sutured so that blood could flow therein. In contrast, the wounded part of the control mouse continued to bleed.

EXAMPLE 6

To 10 ml of human blood was added an equal amount of phosphate buffered saline (pH 7.4) containing 154 mM NaCl, and the resulting mixture was subjected to sucrose density gradient (1.077 g/l) centrifugation at 1,800 rpm, 20° C. for 20 minutes to separate lymphocytes. The lymphocytes were mixed with 50 ml of the same buffer and subjected to centrifugation (1,600 rpm) at 4° C. for 5 minutes to remove impurities. To 100 µl of lymphocyte solution ($3\times10^5$ cells/ml) were added 50 µl of casein kinase II solution (10 mM, 1 mM or 0.1 mM) and 50 µl of $^3$H-thymidine. The resulting mixture was allowed to stand at room temperature for 3 days, and the radioactivity was measured every day. For comparison, a mixture of concanavalin A ("Con A") (10 µg/ml) and interleukin-2 ("IL-2") (50 IU/ml) was used instead of casein kinase II (CK-II) solution.

The results are shown in Table 1.

TABLE 1

|  | 1 day | 2 days | (Unit: cpm) 3 days |
| --- | --- | --- | --- |
| Blank | 517 | 319 | 485 |
| Con A + IL-2 | 434 | 26,854 | 66,108 |
| 10 mM CK-II | 478 | 361 | 500 |
| 1 mM CK-II | 406 | 411 | 441 |
| 0.1 mM CK-II | 370 | 293 | 400 |

As can be seen from Table 1, casein kinase II does not affect the proliferation of lymphocytes.

As described in the above, the hemostatic composition according to the present invention containing thrombin, casein kinase II and sphingosine forms more fibrin clot in a shorter period of time than the conventional hemostatic composition containing thrombin only. Moreover, the composition according to the present invention shows a hemostatic activity as well as tissue suture activity.

Accordingly, the composition of the present invention can be used for hemostasis or hemopexis outside the living body as well as inside the living body, for example treating ulcers. Further, it can be used to treat hemophilia, or as an aid for treating hemophilia. Moreover, it can be used as a hemostatic composition as well as an aid for the conventional hemostatic compositions. It also can be used for suture of wounded blood vessel, as well as inhibitor for growth of bacteria fungi or virus.

We claim:

1. A hemostatic composition comprising thrombin in an amount of at least about 0.1 NIHU/ml, casein kinase-II in an amount of about 0.01 mU/ml to about 1.0 mU/ml, and sphingosine or a sphingosine derivative in an amount of about 10 ng/ml to about 100 ng/ml.

2. The composition of claim 1, which comprises sphingosine.

3. A pharmaceutical composition comprising thrombin in an amount of at least about 0.1 NIH U/ml, casein kinase-II in an amount of about 0.01 mU/ml to about 1.0 mU/ml, and sphingosine or a sphingosine derivative in an amount of about 10 ng/ml to about 100 ng/ml, in an anti-ulcer effective, hemostatic effective, blood vessel suturing effective, or microorganism growth inhibiting amounts, and a pharmaceutically acceptable carrier.

4. The pharmaceutical composition of claim 3 which comprises sphingosine.

5. A method for treating ulcers in a patient comprising administering to the patient an anti-ulcer effective amount of the composition of claim 3.

6. A method for effecting hemostasis in a patient comprising administering to the patient the composition of claim 3.

7. A method for suturing a blood vessel in a patient which comprises administering to the patient a blood vessel suturing effective amount of the composition of claim 3.

8. A method for treating hemophilia in a patient which comprises administering a hemophilia-symptom inhibiting amount of the composition of claim 3.

9. A method for inhibiting the growth of microorganisms in a patient comprising administering a microorganisms growth inhibiting effective amount of the composition of claim 3.

* * * * *